United States Patent [19]
Torelli et al.

[11] 4,395,408
[45] Jul. 26, 1983

[54] NOVEL STEROIDS

[75] Inventors: Vesperto Torelli, Maisons-Alfort; Roger Deraedt, Pavillons-sous-Bois; Lucien Nedelec, Le Raincy, all of France

[73] Assignee: Roussel Uclaf, Paris, France

[21] Appl. No.: 292,794

[22] Filed: Aug. 14, 1981

[30] Foreign Application Priority Data

Nov. 21, 1980 [FR] France ................. 80 24749

[51] Int. Cl.³ .............. C07J 5/00; A01N 45/00; C07C 117/00
[52] U.S. Cl. .................. 424/238; 260/349; 260/397; 260/397.3; 260/397.5
[58] Field of Search .......... 260/397.3, 397.5, 349; 424/238

[56]  References Cited
U.S. PATENT DOCUMENTS 3,102,895  9/1963  Mainil ........................... 260/397.3

Primary Examiner—Elbert L. Roberts
Attorney, Agent, or Firm—Hammond & Littell, Weissenberger and Muserlian

[57] ABSTRACT

Novel 3-amino-steroids of the formula

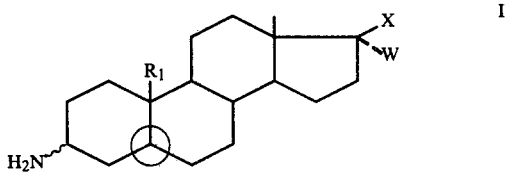

wherein $R_1$ is selected from the group consisting of hydrogen and methyl, W is selected from the group consisting of hydrogen and —OH and taken together with x forms ethylidene, X is selected from the group consisting of ethyl,

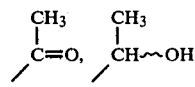

and taken together with W forms ethylidene and the wavy lines signify that the substituents are in the α or β-position with the proviso that when $R_1$ is methyl and X is ethyl,

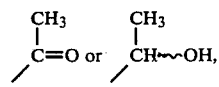

W is —OH and their non-toxic, pharmaceutically acceptable acid addition salts and their preparation and intermediates therefore capable of stimulating immunitary activity.

13 Claims, No Drawings

NOVEL STEROIDS

STATE OF THE ART

Related prior art are U.S. Pat. No. 3,196,169 and Bull. Soc. Chim. France, Vol. No. 10 (1967) and C. R. Acad Sciences Paris, Vol. 260 (Jan. 11, 1965).

OBJECTS OF THE INVENTION

It is an object of the invention to provide the novel compounds of formula I and their non-toxic, pharmaceutically acceptable acid addition salts and a process for their preparation.

It is another object of the invention to provide novel compositions and a novel method for the treatment of autoimmuno maladies.

These and other objects and advantages of the invention will become obvious from the following detailed description.

THE INVENTION

The novel compounds of the invention are selected from the group consisting of 3-amino-steroids of the formula

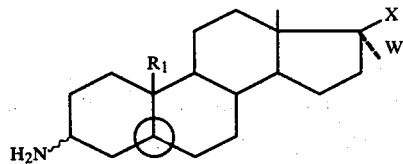

wherein $R_1$ is selected from the group consisting of hydrogen and methyl, W is selected from the group consisting of hydrogen and —OH and taken together with X forms ethylidene, X is selected from the group consisting of ethyl,

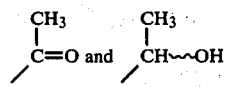

and taken together with W forms ethylidene and the wavy lines signify that the substituents are in the α or β-position with the proviso that when $R_1$ is methyl and X is ethyl,

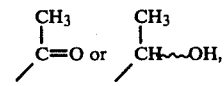

W is —OH and their non-toxic, pharmaceutically acceptable acid addition salts. The compounds of formula I can exist in their separate isomeric forms or as mixtures of isomers.

Examples of suitable acids for the preparation of the non-toxic, pharmaceutically acceptable acid addition salts are inorganic acids such as sulfuric acid, hydrochloric acid, hydrobromic acid, nitric acid, hydroiodic acid and phosphoric acid and organic acids such as formic acid, acetic acid, benzoic acid, maleic acid, fumaric acid, succinic acid, tartaric acid, citric acid, oxalic acid, glyoxylic acid, aspartic acid, alkane sulfonic acids such as methane sulfonic or ethane sulfonic acids and arylsulfonic acids such as benzene sulfonic and paratoluene sulfonic acids, and arylcarboxylic acids.

Among the preferred compounds of the invention are those of formula I wherein X is

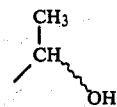

and among those compounds those wherein $R_1$ is hydrogen and X is

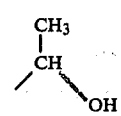

and their non-toxic, pharmaceutically acceptable acid addition salts. Especially preferred are (20S) 3α-amino-19-nor-15α-pregnane-20-ol and (20S) 3β-amino-19-nor-5α-pregnane-20-ol and their non-toxic, pharmaceutically acceptable acid addition salts.

The novel process of the invention for the preparation of a compound of formula I comprises reducing an azide of the formula

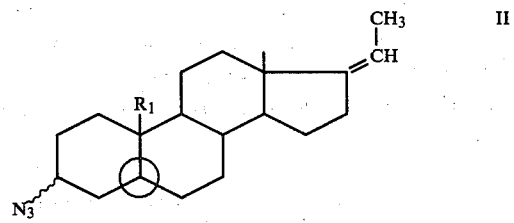

wherein $R_1$ has the above definition to obtain an amine of the formula

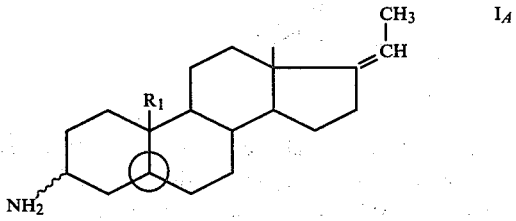

wherein $R_1$ has the above definition which is a compound of formula 1 when X and W form ethylidene which may be isolated and salified if desired or reduced to obtain a compound of the formula

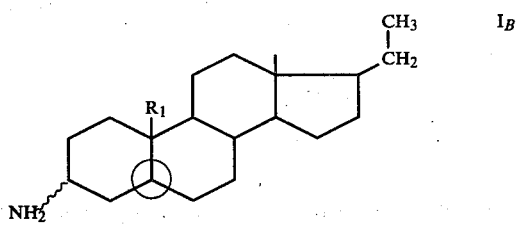

wherein $R_1$ has the above definition which may be isolated and salified, if desired, or the compound of formula $I_A$ is hydrated to obtain a compound of the formula

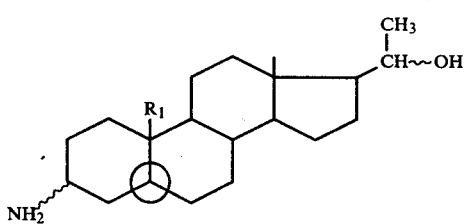

wherein $R_1$ has the above definition which may be isolated and salified, if desired, or subjecting the latter to oxidation to obtain a compound of the formula

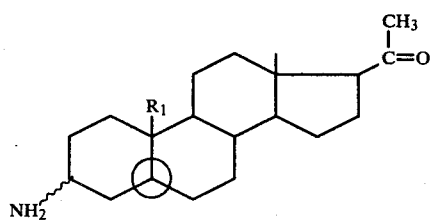

wherein $R_1$ has the above definition which may be isolated and salified, if desired, or reacting the compound of formula $I_A$ with an amine protecting agent capable of attaching R to the amine group to obtain a compound of the formula

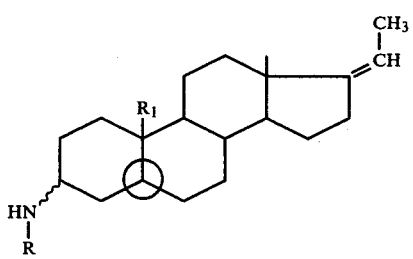

wherein $R_1$ has the above definition and R is an easily cleavable protective group and subjecting the latter to cis dihydroxylation to obtain a compound of the formula

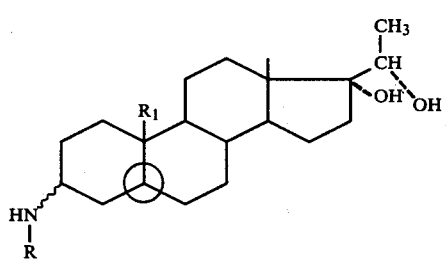

wherein R and $R_1$ have the above definitions and subjecting the latter to an agent capable of cleaving the amino protective group to obtain a compound of the formula

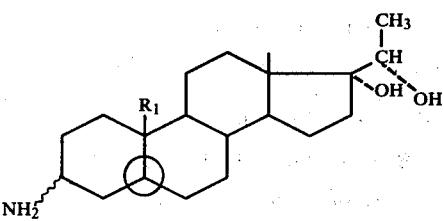

which may be isolated and salified, if desired, or subjecting the compound of formula IV to oxidation to obtain a compound of the formula

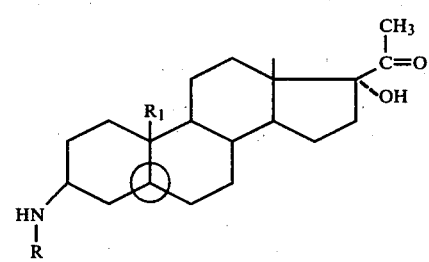

and subjecting the latter to an agent capable of cleaving the amino protecting group to obtain a compound of the formula

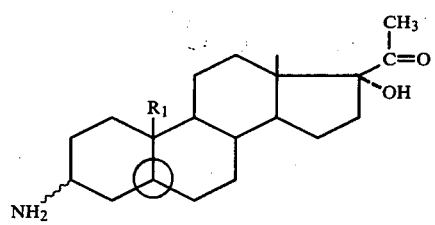

which may isolated and salified, if desired, or reducing a compound of formula V to obtain a compound of the formula

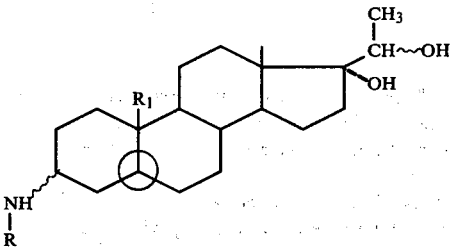

wherein R and $R_1$ have the above definition and subjecting the latter to an agent capable of cleaving the amino protecting group to obtain a compound of the formula

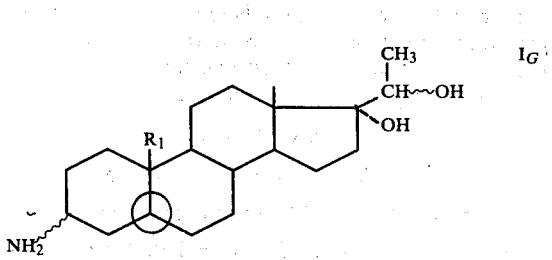

which may be isolated and salified, if desired.

In a preferred mode of the process of the invention, the azide of formula II is reduced with lithium aluminum hydride but equally useful are other metallic hydrides or other reducing agents such as thiols or hydrogen in the presence of a catalyst. The reduction of the amine of formula $I_A$ is preferably a catalytic hydrogenation such as with a rhodium or platinum based catalyst and especially a palladium catalyst such as palladium carbonate.

The hydration of the compound of formula $I_A$ is preferably effected with a diborane formed in situ such as with an alkali metal borohydride like potassium or sodium borohydride to obtain a compound of formula $I_C$ with a (20S) carbon configuration. The diborane used is in the form of a complex such as complex of the formula $BH_3.S—(CH_3)_2$ to obtain a compound of formula $I_C$ with the hydroxyl being in the (R) and (S) configuration in about equal proportions. The reaction with diborane is followed by oxidation such as hydrogen peroxide. The oxidation of compounds of formula $I_C$ and IV is effected by the Oppenauer method with an excess of acetone in the presence of aluminum alkoxide but also useful are other classic oxidants such as chromic acid and its derivatives such as a dichromate.

The cis dihydroxylation of the compounds of formula III is effected after protection of the amino group with trifluoroacetyl by reacting the amine with trifluoroacetic acid anhydride. More generally, the protective agent for the amine function may be a halide or an anhydride capable of attaching the R group. The easily cleavable amino protecting group R may, for example, be an aliphatic, aromatic or heterocyclic acyl or carbamoyl group.

Example of lower alkanoyl groups are formyl, acetyl or propionyl, of lower alkoxy carbonyl or cycloalkoxycarbonyl such as methoxycarbonyl, ethoxycarbonyl, propoxycarbonyl or tert.-butoxycarbonyl and aroyl such as benzoyl or aralkoxycarbonyl such as benzyloxycarbonyl. The said acyl group may be substituted such as with chlorine, bromine, iodine or fluorine, especially trifluoroacetyl. R may also be ar-lower alkyl such as benzyl.

The cleavage of R may be effected by hydrolysis with a base or an acid or with hydrazine. Acidic hydrolysis is preferred to eliminate alkoxycarbonyl or cycloalkoxycarbonyl groups such as tert.-butyloxycarbonyl or optionally substituted aralkoxycarbonyl such as benzyloxycarbonyl. Basic hydrolysis is preferred for the elimination or acyl groups such as trifluoroacetyl and hydrazine hydrolysis is preferred for removing groups such as phthalyl. Hydrogen in the presence of a catalyst is preferred for the removal of benzhydryl, benzyl or benzyloxycarbonyl groups. Other known methods for the removal of protective groups may also be used.

Among the preferred groups for R are acetyl and especially trifluoroacetyl.

The cis dihydroxylation of the compound of formula III is preferably effected with an acid anhydride such as osmic anhydride in the presence of an amine oxide, especially trimethyloxamine or triethyloxamine but it may also be effected, for example, by formation of an osmate with osmic anhydride in stoichiometric proportions followed by reduction with a bisulfite for example or by oxidation with a chlorate such as barium chlorate.

The reduction of the compounds of formula V may be effected with an alkali metal borohydride such as sodium or potassium borohydride when it is preferred to obtain a compound of formula $I_G$ with a hydroxyl of (R) configuration or with an alkali metal such as sodium or potassium in an alkanol such as ethanol when it is preferred to obtain a compound of formula $I_G$ with a hydroxyl of (S) configuration.

The products resulting from the process of the invention may be in the form of individual isomers or mixtures of the said isomers. The isomers may be separated from the mixtures by classical methods such as crystallization.

A variation of the process of the invention comprises subjecting a compound of formula $I_A$ to a cis-dihydroxylation to obtain a compound of formula $I_E$ which may be isolated and salified, if desired, or subjected to oxidation to obtain a compound of formula $I_F$ which may be isolated and salified, if desired, or reduced to obtain a compound of formula $I_G$ which may be isolated and salified.

The said cis-dihydroxylation, the oxidation and reduction steps of the variation may be effected under the conditions described above for the compounds of formulae III, $I_C$ and V.

The compounds of formula I have a basic character and the acid addition salts may be formed by reacting approximately stoichiometric proportions of the acid and the compounds of formula I which need not be isolated.

The novel compositions of the invention for the treatment of autoimmuno maladies are comprised of at least one compound selected from the group consisting of a compound of formula I and their non-toxic, pharmaceutically acceptable acid addition salts and an inert pharmaceutical carrier or excipient. The compositions may be in the form of tablets, dragees, gelules, granules, suppositories and injectable solutions or suspensions.

Examples of suitable excipients are talc, arabic gum, lactose, starch, magnesium stearate, cacao butter, aqueous or non-aqueous vehicles, fatty bodies of vegetable or animal origin, paraffinic derivatives, glycols, diverse wetting agents, emulsifiers or dispersants and preservatives.

The compositions are useful for the treatment of autoimmuno maladies resulting from a deficiency of certain lymphocytes such as maladies of conjunctive tissue which are non-specific of an organ such as rhumatoidal arthritis or systemic erythematous lupus or specific maladies of an organ such as thyroiditis, pymphygus or hemolytic anaemia. The compositions are also useful as adjuvant treatment of anticancer chemotherapy and antibiotherapy.

Among the preferred compositions of the invention are those wherein X is

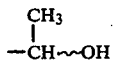

and among these compounds those wherein $R_1$ is hydrogen and X is

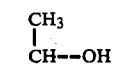

and their non-toxic, pharmaceutically acceptable acid addition salts. Especially preferred are (20S) 3α-amino-19-nor-5α-pregnane-20-ol and (20S) 3β-amino-19-nor-5α-pregnane-20-ol and their non toxic, pharmaceutically acceptable acid addition salts.

The novel method of the invention of treating autoimmuno maladies in warm-blooded animals, including humans, comprises administering to warm-blooded animals an amount sufficient to treat autoimmuno maladies of at least one compound selected from the group consisting of a compound of formula I and their non-toxic, pharmaceutically acceptable acid addition salts. The compounds may be administered orally, rectally or parenterally. The usual daily dose is depending on the affection being treated, the patient and the method of administration. There may be 0,02 to 2 mg/kg per day of the product of example 4 when administered orally in the adult, as adjuvant treatment of antibiotherapy.

The novel intermediate products of the invention are those of formula II which may be prepared by reacting a compound of the formula

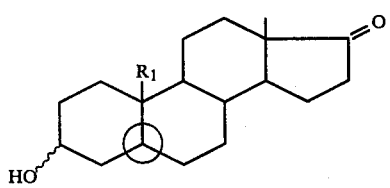

wherein $R_1$ has the above definition with an excess of ethyl triphenyl-phosphonium bromide and potassium tert.-butylate to obtain a compound of the formula

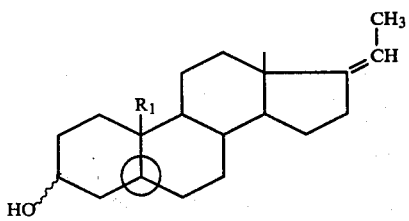

wherein $R_1$ has the above definition and transforming the latter to an azide of formula II corresponding to the alcohol, for example by passage through the tosylate then reaction with sodium azide or directly by reaction with diphenyl azidophosphate in the presence of ethyl azodicarboxylate and triphenylphosphine. The transformation of the compound of formula VIII into the azide is effected with an inversion of the 3-configuration, for example, the α-alcohol leads to a β-azide and vice versa and an α,β-mixture leads to an α,β-mixture of inverse proportions.

In the following examples there are described several preferred embodiments to illustrate the invention. However, it should be understood that the invention is not intended to be limited to the specific embodiments.

EXAMPLE 1

(Z) 3α-amino-$\Delta^{17(20)}$-5α-pregnene hydrochloride

STEP A: (Z) $\Delta^{17(20)}$-5α-pregnene-3β-ol

A mixture of 59.4 g of triphenylethylphosphonium bromide, 16.1 g of potassium tert.-butylate and 160 ml of tetrahydrofuran was stirred for 30 minutes and after the addition of 23.2 g of epiandrosterone, the mixture was stirred for 15 hours and was poured into iced water. The mixture was extracted with ethyl acetate and the organic phase was washed with water, dried and evaporated to dryness. The residue was chromatographed over silica gel and was eluted with a 7-3 cyclohexane-ethyl acetate mixture. The eluant was evaporated to dryness and the residue was taken up in methanol. The iced solution was vacuum filtered and the product was dried in air to obtain 23.1 g of (Z) $\Delta^{17(20)}$-5α-pregnene-3β-ol melting at 160° C.

STEP B: (Z) 3α-azido-$\Delta^{17(20)}$-5α-pregnene 1.92 g of ethyl azodicarboxylate and 3.02 g of diphenyl azidophosphate were added to a solution of 1.66 g of the product of Step A in 30 ml of benzene and 5 ml of tetrahydrofuran and the mixture was stirred in an ice bath while adding thereto over 20 minutes a solution of 2.88 g of triphenylphosphine in 30 ml of benzene. The mixture was stirred at 10° C. for 40 minutes and was washed with water, dried and evaporated to dryness. The residue was chromatographed over silica gel and was eluted with heptane and then with a 1-1 heptane-acetone mixture to obtain after distillation 1.67 g of (Z) 3α-azido-$\Delta^{17(20)}$-5α-pregnene in the form of crystals melting at 114° C. after crystallization from methanol.

STEP C: (Z) 3α-amino-$\Delta^{17(20)}$-5α-pregnene hydrochloride 14.5 g of the product of Step B were dissolved at 25°–27° C. in 290 ml of tetrahydrofuran and then 800 mg of lithium aluminum hydride were added to the mixture in an ice bath over one hour. The mixture was stirred for one hour and methanol was added to remove excess hydride. The mixture was filtered and the filtrate was washed with an aqueous Seignette salt solution, then with a saturated sodium hydroxyde solution, dried and evaporated to dryness to obtain 13.1 g of (Z) 3α-amino-$\Delta^{17(20)}$-5α-pregnene in the form of crystals melting at ≃90° C. The said product was dissolved in 150 ml of ethyl acetate and 30 ml of methylene chloride and 27 ml of 1.7 N hydrogen chloride in ethyl acetate were added thereto. The mixture was vacuum filtered and the product was washed and dried under reduced pressure to obtain 13.2 g of (Z) 3α-amino-$\Delta^{17(20)}$-5α-pregnene hydrochloride in the form of crystals melting at >300° C. and having a specific rotation of $[\alpha]_D^{20} = +38.5° \pm 1.5°$ (c=1% in pyridine containing 10% in water).

EXAMPLE 2

(Z) 3β-amino-$\Delta^{17(20)}$-5α-pregnene

Using the procedure of Example 1, androsterone was reacted to obtain (Z) 3β-amino-$\Delta^{17(20)}$-5α-pregnene melting at 110° C. after crystallization from methanol.

EXAMPLE 3

(20S)3α-amino-5α-pregnane-17α,20-diol hydrochloride

STEP A:

N-[(Z)Δ$^{17(20)}$-5α-pregnene-3α-yl]-trifluoroacetamide 16.5 ml of trifluoroacetic acid anhydride were added over 5 minutes under an inert atmosphere at 5° C. to a suspension of 1.65 g of the product of Example 1, 165 ml of methylene chloride and 16.5 ml of pyridine and the mixture was stirred at room temperature for 15 minutes and was evaporated to dryness under reduced pressure. 200 ml of water were added to the residue and the mixture was vacuum filtered. The product was washed with water and dried under reduced pressure to obtain 18.1 g of N-[(Z)Δ$^{17(20)}$-5α-pregnene-3α-yl]trifluoroacetamide in the form of crystals melting at 204° C.

STEP B:

N-[(20S)5α-pregnane-17α,20-diol-3α-yl]-trifluoroacetamide 9 g of the N-oxide of trimethylamine dihydrate and a solution of 360 mg of osmium tetraoxide in 71 ml of methyl ethyl ketone were added under an inert atmosphere to a solution of 18.1 g of the product of Step A in 100 ml of methyl ethyl ketone and the mixture was refluxed for 2 hours and then allowed to cool. 200 ml of a solution of 10% sodium thiosulfate in water were added to the mixture which was stirred at room temperature for 30 minutes. The decanted organic phase was washed with water, dried over magnesium sulfate, filtered and evaporated to dryness under reduced pressure. The oil residue was chromatographed over silica gel and was eluted with a 7-3 benzene-ethyl acetate mixture to obtain 14 g of N-[(20S)5α-pregnane-17α,20-diol-3α-yl]-trifluoroacetamide melting at 172° C., then 192° C.

STEP C: (20S) 3α-amino-5α-pregnane-17α,20-diol hydrochloride 8 ml of sodium hydroxide solution were added under an inert atmosphere to a solution of 4 g of the product of Step B in 20 ml of methanol and the mixture was stirred for 90 minutes. 50 ml of water were added to the mixture which was then stirred for 10 minutes and vacuum filtered. The product was washed with water and dried at 40° C. under reduced pressure to obtain 3 g of (20S) 3α-amino-5α-pregnane-17α,20-diol melting at 210° C.

3 g of the said product were dissolved in 30 ml of methanol and 1.7 N hydrogen chloride in ethyl acetate were added thereto to adjust the pH to 1. The mixture was concentrated under reduced pressure to a volume of 10 ml. 30 ml of ethyl acetate were added to the mixture which was allowed to stand for 30 minutes and was vacuum filtered. The product was crystallized from methanol to obtain 2.6 g of (20S) 3α-amino-5α-pregnane-17α,20-diol hydrochloride melting at 300° C.

Analysis: $C_{21}H_{38}NO_2Cl$; molecular weight=371.98. Calculated: %C 67.80; %H 10.30; %N 3.77; %Cl 9.53. Found: %C 67.7; %H 10.3; %N 3.6; %Cl 9.5.

EXAMPLE 4

(20S) 3α-amino-19-nor-5α-pregnane-20-ol hydrochloride

Using the procedure of Example 1, 5α-estran-3β-ol-17-one (German Pat. No. 864,257) was reacted to obtain (Z) 3α-amino-19-nor-Δ$^{17(20)}$-5α-pregnene. A solution of 0.5 ml of boron trifluoride-etherate in 2.5 ml of tetrahydrofuran was added dropwise at 5° C. under nitrogen to a suspension of 156 mg of sodium borohydride in 5 ml of tetrahydrofuran and the mixture was stirred in an ice bath for one hour. A solution of 296 mg of (Z) 3α-amino-19-nor-Δ$^{17(20)}$-5α-pregnene in 3 ml of tetrahydrofuran was added to the mixture which was stirred at room temperature for 90 minutes and then cooled in an ice bath. 2 ml of 6 N sodium hydroxide solution were slowly added to the mixture which was stirred at room temperature for 5 minutes. The decanted aqueous phase was extracted with tetrahydrofuran and the organic phase was washed and 4 ml of 5 N sodium hydroxide and 2 ml of water oxygenated to 110 volumes were added thereto. The mixture was stirred for 45 minutes and was extracted with ethyl acetate. The organic phase was washed, dried and evaporated to dryness under reduced pressure and the dry residue was taken up in 10 ml of methanol and 5 ml of N hydrochloric acid. The mixture was heated in a water bath at 50° C. for 30 minutes and was poured into aqueous saturated sodium bicarbonate solution. The mixture was extracted with methylene chloride and the organic phase was washed, dried and evaporated to dryness under reduced pressure to obtain 257 mg of (20S) 3α-amino-19-nor-5α-pregnane-20-ol in the form of crystals melting at ≃190° C.

A solution of 1.73 g of the said product in 25 ml of methanol was admixed with 3 ml of 2 N methanolic hydrogen chloride solution. The mixture was concentrated and diluted with ethyl acetate and concentrated again. The mixture was iced and vacuum filtered and the product was washed and dried to obtain 1.78 g of (20S)3α-amino-19-nor-5α-pregnane-20-ol-hydrochloride.

EXAMPLE 5

(20S)3β-amino-19-nor-5α-pregnane-20-ol hydrochloride

Using the procedure of Examples 1 and 4, 5α-estran-3α-ol-17-one was reacted to obtain (20S) 3β-amino-19-nor-5α-pregnane-20-ol melting at 177° C. after crystallization from 50% aqueous isopropanol, which was converted into its hydrochloride.

NMR Spectrum (pyridine): Peaks at 3.8 ppm (3α-hydrogen); at 0.65 ppm (hydrogen of 13-methyl); at 1.27-1.39 ppm (hydrogen of 20-methyl).

EXAMPLE 6

3α-amino-5α-pregnane-17α-ol-20-one hydrochloride

The product of Step B of Example 3 was oxidized to obtain N-(5α-pregnane-17α-ol-20-one-3α-yl)-trifluoroacetamide melting at 178° C. and then 186° C. The latter was treated as in Step C of Example 3 to obtain first 3α-amino-5α-pregnane-17α-ol-20-one melting at 216° C. which was converted into its hydrochloride melting at >300° C. after crystallization from ethyl acetate and having a specific rotation of $[\alpha]_D^{20}$ = +25.5°±1.5° (c=1% in water).

EXAMPLE 7

Tablets were prepared containing 10 mg of (20S) 3α-amino-19-nor-5α-pregnane-20-ol hydrochloride or 20 mg of (20S) 3β-amino-19-nor-5α-pregnane-20-ol hydrochloride and sufficient excipient of talc, lactose, starch and magnesium stearate to obtain a final tablet of 100 mg.

PHARMACOLOGICAL DATA

A. Adjuvant for Anaphylactic Shock

The administration to animals of a compound capable of stimulating the activity of immunitary systems leads to an increase in shock in response to administration of antigen to which the animal is senitive. Male mice weighing between 30 to 35 g were sensitized by intraplantary administration of beef seric albumin. 8 days later, the mice received intraveinously an antigen and under the minimum sensibilization conditions, the control animals were not in mortal shock at the time of the last administration.

The test compound was injected intraplantary admixed with an antigen and if the product was an adjuvant, it increased the sensibilization and resulted in mortal shock with an intraveinous administration. The active dose which provoked a mortality equal to or greater than 50% of the animals was determined and the results are reported in Table I.

TABLE I

| Example No. | Dose in mg per animal |
|---|---|
| 1 | 0.5 |
| 3 | ≧2 |
| 4 | 0.5 |
| 5 | 0.5 |
| 6 | 2 |

B. Acute Toxicity

The acute toxicity was determined as the lethal dose LD0 by orally and intraperitoneally administering the test compounds to mice and the maximum dose which did not cause any mortality after 8 days was determined. The results are reported in Table II.

TABLE II

| | DL0 in mg/kg | |
|---|---|---|
| Example No. | oral | I.P. |
| 1 | ≧400 | 100 |
| 3 | 200 | 60 |
| 5 | 400 | 100 |
| 6 | ≧400 | 60 |

Various modifications of the compounds and process of the invention may be made without departing from the spirit or scope thereof and it is to be understood that the invention is intended to be limited only as defined in the appended claims.

What we claim is:

1. A compound selected from the group consisting of (Z) 3α-amino-$\Delta^{17(20)}$-5α-pregnene, (20S) 3α-amino-19-nor-5α-pregnane-20-ol and (20S) 3β-amino-19-nor-5α-pregnane-20-ol and their non-toxic, pharmaceutically acceptable acid addition salts.

2. A compound of claim 19 selected from the group consisting of (Z) 3α-amino-$\Delta^{17(20)}$-5α-pregnene and its non-toxic, pharmaceutically acceptable acid addition salts.

3. A compound of claim 1 selected from the group consisting of (20S) 3α-amino-19-nor-5α-pregnane-20-ol and its non-toxic, pharmaceutically acceptable acid addition salts.

4. A compound of claim 1 selected from the group consisting of (20S) 3β-amino-19-nor-5α-pregnane-20-ol and its non-toxic, pharmaceutically acceptable acid addition salts.

5. A compound having the formula of

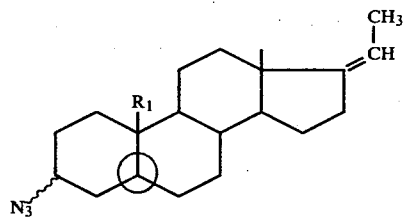

wherein $R_1$ is selected from the group consisting of hydrogen and methyl and the wavy line indicates the α- or β-position.

6. A composition for the treatment of auto immuno maladies resulting from a deficiency of lymphocytes or malady of an organ comprising an amount of at least one compound of claim 1 in an amount sufficient to treat autoimmuno maladies and an inert carrier.

7. A composition of claim 6 wherein the active compound is selected from the group consisting of (20S) 3α-amino-19-nor-5α-pregane-20-ol and its non-toxic, pharmaceutically acceptable acid addition salts.

8. A composition of claim 6 wherein the active compound is selected from the group consisting of (20S) 3β-amino-19-nor-5α-pregnane-20-ol and its non-toxic, pharmaceutically acceptable acid addition salts.

9. A method of treating autoimmuno maladies resulting from a deficiency of lymphocytes or malady of an organ in warm-blooded animals comprising administering to warm-blooded animals an amount sufficient to treat autoimmuno maladies of at least one compound of claim 1.

10. A method of claim 9 wherein the active compound is selected from the group consisting of (20S) 3α-amino-19-nor-5α-pregane-20-ol and its non-toxic, pharmaceutically acceptable acid addition salts.

11. A method of claim 9 wherein the active compound is selected from the group consisting of (20S) 3β-amino-19-nor-5α-pregnane-20-ol and its non-toxic, pharmaceutically acceptable acid addition salts.

12. A composition of claim 6 wherein the compound is selected from the group consisting of (Z) 3α-amino-$\Delta^{17(20)}$-5α-pregnene and its non-toxic, pharmaceutically acceptable acid addition salts.

13. The method of claim 9 wherein the compound is selected from the group consisting of (Z) 3α-amino-$\Delta^{17(20)}$-5α-pregnene and its non-toxic, pharmaceutically acceptable acid addition salts.

* * * * *

UNITED STATES PATENT AND TRADEMARK OFFICE
CERTIFICATE OF CORRECTION

PATENT NO. : 4,395,408
DATED : July 26, 1983
INVENTOR(S) : VESPERTO TORELLI ET AL.

It is certified that error appears in the above-identified patent and that said Letters Patent is hereby corrected as shown below:

Column 5, line 47: "cycloalkox-" should read
-- cycloalkoxy- --.
Column 5, line 48 and 51: "ycarbonyl" should read
-- carbonyl --.
Column 5, line 50: "benzylox-" should read -- benzyloxy- --.
Column 11, line 1 of claim 2: "claim 19" should read
-- claim 1 --.

*Signed and Sealed this*

*Twenty-fifth* Day of *September 1984*

[SEAL]

*Attest:*

GERALD J. MOSSINGHOFF

*Attesting Officer*   *Commissioner of Patents and Trademarks*